(12) United States Patent
Bao et al.

(10) Patent No.: US 12,310,530 B2
(45) Date of Patent: May 27, 2025

(54) AUTOMATIC MAIN INGREDIENT EXTRACTION FROM FOOD RECIPE

(71) Applicant: KONINKLIJKE PHILIPS N.V., Eindhoven (NL)

(72) Inventors: Wei Shun Bao, Shanghai (CN); Weimin Xiao, Shanghai (CN); Yun Chen, Shanghai (CN)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 976 days.

(21) Appl. No.: 17/267,053

(22) PCT Filed: Aug. 19, 2019

(86) PCT No.: PCT/EP2019/072151
§ 371 (c)(1),
(2) Date: Feb. 9, 2021

(87) PCT Pub. No.: WO2020/043528
PCT Pub. Date: Mar. 5, 2020

(65) Prior Publication Data
US 2021/0212505 A1    Jul. 15, 2021

(30) Foreign Application Priority Data

Aug. 27, 2018  (WO) ................. PCT/CN2018/102583
Oct. 18, 2018  (EP) ..................................... 18201150
Mar. 19, 2019  (WO) ................. PCT/CN2019/078721

(51) Int. Cl.
*A47J 36/32*   (2006.01)
*A47J 37/06*   (2006.01)
(Continued)

(52) U.S. Cl.
CPC ............ *A47J 36/32* (2013.01); *A47J 37/0641* (2013.01); *F24C 7/002* (2013.01); *G01N 33/02* (2013.01)

(58) Field of Classification Search
CPC .......................... G01N 33/02; A23V 2300/18; A23V 2002/00; A47J 36/32; A47J 37/0641; F24C 7/002
(Continued)

(56) References Cited

U.S. PATENT DOCUMENTS 9,690,847 B2   6/2017   Kaneda
9,754,508 B2   9/2017   Shahar
(Continued)

FOREIGN PATENT DOCUMENTS

CN   107065634 A    8/2017
CN   107249403 A   10/2017
(Continued)

OTHER PUBLICATIONS

International Search Report and Written Opinion Dated Sep. 23, 2019 for International Application No. PCT/EP2019/072151 Filed Aug. 19, 2019.
(Continued)

*Primary Examiner* — Emily E Larocque
(74) *Attorney, Agent, or Firm* — Maschoff Brennan (57) ABSTRACT

Provided is a system (100) for determining the main ingredients of a food recipe. The system comprises a first input (102) for receiving the identity and mass fraction ($w_{ri}$) of each ingredient (i) in the food recipe (r), and a second input (104) for receiving the identity of ingredients of each known recipe of a population of known recipes. The system further includes a controller (106) configured to calculate, for each ingredient (i), the fraction ($P(i)$) of the population which uses the ingredient. The controller then calculates, using the fraction ($P(i)$) and the mass fraction ($w_{ri}$), a value ($V_{ri}$)
(Continued)

which positively correlates with the mass fraction ($w_{ri}$) and negatively correlates with the fraction (P(i)). The main ingredients are then determined according to the ingredients which have values ($V_{ri}$) equal to or greater than a threshold value. Further provided is a cooking appliance (200) which includes the system, a computer implemented method for determining the main ingredients of a food recipe, and a computer program which implements the method.

15 Claims, 4 Drawing Sheets

(51) Int. Cl.
*F24C 7/00* (2006.01)
*G01N 33/02* (2006.01)

(58) Field of Classification Search
USPC .......................................................... 708/133
See application file for complete search history.

(56) References Cited

U.S. PATENT DOCUMENTS

| | | | |
|---|---|---|---|
| 9,811,593 B2 | 11/2017 | Uchida | |
| 2014/0272026 A1* | 9/2014 | Wallace | G01G 19/00 177/25.13 |
| 2015/0366405 A1* | 12/2015 | Manchuliantsau | A61B 5/0205 222/23 |
| 2016/0081515 A1 | 3/2016 | Aboujassoum | |
| 2017/0046980 A1 | 2/2017 | Mehta | |

FOREIGN PATENT DOCUMENTS

| | | |
|---|---|---|
| CN | 107466219 A | 12/2017 |
| CN | 108338650 A | 7/2018 |
| DE | 102016123655 A1 | 6/2018 |
| EP | 3143914 | 3/2017 |
| IN | 7815DELNP2012 A | 3/2014 |
| WO | 2011100896 A1 | 8/2011 |

OTHER PUBLICATIONS

Wikipedia, "Information content" https://en.wikipedia.org/wiki/Self-information.

Wikipedia, "Cross entropy" https://en.wikipedia.org/wiki/Cross_entropy.

Forbes, et al: Content-boosted matrix factorization for recommender systems: experiments with recipe recommendation:, Proceedings of the fifth ACM conference on Recommender systems. ACM, 2011.

Google, "word2vec", 2013 https://code.google.com/archive/p/word2vec/.

* cited by examiner

AUTOMATIC MAIN INGREDIENT EXTRACTION FROM FOOD RECIPE

CROSS REFERENCE TO RELATED APPLICATIONS

This application is the U.S. National Phase application under 35 U.S.C. § 371 of International Application No. PCT/EP2019/072151 filed Aug. 19, 2019, which claims the benefit of European Patent Application Number 18201150.2 filed Oct. 18, 2018 and Patent Application Number PCT/CN2018/102583 filed Aug. 27, 2018 and Patent Application Number PCT/CN2019/078721 filed Mar. 19, 2019. These applications are hereby incorporated by reference herein.

FIELD OF THE INVENTION

This invention relates to a system and method for determining the main ingredients of a food recipe.

BACKGROUND OF THE INVENTION

Controlling cooking parameters, such as the temperature at which food ingredients are cooked and the duration of cooking, is important to ensure that the prepared dish is both safe and pleasurable to consume.

A key factor in selection of such cooking parameters is what ingredients are included in the food recipe. In particular, the cooking parameters tend to be selected on the basis of the main ingredients of the recipe, rather than on every single ingredient. The reason for this is that there may be certain minor or incidental ingredients which should not influence the selection of cooking parameters. Moreover, when the selection of cooking parameters is carried out computationally, basing such a selection on a complete list of ingredients may use more computational resources than if the calculation is instead based only on the main ingredients of the recipe.

Distinguishing the main ingredients from such minor ingredients is a challenge, particularly when the determination of the main ingredients is carried out in an automated manner. This is because such a determination may only take account of the mass fractions of each ingredient. Such mass fraction information alone may not lead to an accurate identification of the main ingredients. For example, the salmon in a salmon salad may not be identified as a main ingredient on the basis of the mass fraction of salmon in the recipe, but the salmon nevertheless may correspond to a main ingredient.

Moreover, for more elaborate recipes, such as those used in restaurants, which include more ingredients, it may be challenging to identify from a list of ingredients placed in order of mass percentage in the recipe the point at which the main ingredients are separated from the minor ingredients.

Basing the selection of cooking parameters on an inaccurate main ingredient determination may lead to a dissatisfactory outcome in terms of the prepared dish. For example, inaccurate determination of the main ingredients may mean that the correspondingly poor selection of cooking parameters results in the prepared dish being undercooked or overcooked.

SUMMARY OF THE INVENTION

The invention is defined by the claims.

According to an aspect there is provided a system for determining the main ingredients of a food recipe, the system comprising:
a first input for receiving the identity and mass fraction ($w_{ri}$) of each ingredient (i) in the food recipe (r);
a second input for receiving the identity of ingredients of each known recipe of a population of known recipes; and
a controller configured to:
calculate, for each ingredient (i), the fraction (P(i)) of the population which uses the ingredient;
calculate, using the fraction (P(i)) and the mass fraction ($w_{ri}$), a value ($V_{ri}$) which positively correlates with the mass fraction ($w_{ri}$) and negatively correlates with the fraction (P(i)); and
determine the main ingredients according to the ingredients which have values ($V_{ri}$) equal to or greater than a threshold value.

The system enables more accurate determination of the main ingredients of a recipe, e.g. in comparison to a determination which only makes use of the mass percentages of the ingredients. This more accurate main ingredient determination, in turn, enables more precise tailoring of cooking parameters, such as the temperature at which food ingredients are cooked and the duration of cooking, to the recipe. Such superior tailoring of the cooking parameters to the recipe may reduce the risk of the final dish being undercooked or overcooked.

Moreover, determining the nutritional composition of the recipe may be based on the determined main ingredients, rather than on every single ingredient in the recipe, such as to save on computational resources. Since the system enables more accurate determination of the main ingredients, the nutritional composition calculation may be both efficient and accurate.

The system makes use of both the mass fraction ($w_{ri}$) of each ingredient (i) in a given recipe and the fraction (P(i)) of the population of known recipes which uses each ingredient (i) to determine the value ($V_{ri}$). For each ingredient (i), the mass fraction ($w_{ri}$) and the fraction (P(i)) of the population will both be greater than 0 but less than 1. The value ($V_{ri}$) positively correlates with the mass fraction in view of the fact that, to a first approximation, a greater mass fraction ($w_{ri}$) of an ingredient in a recipe will tend to increase the likelihood of that ingredient corresponding to a main ingredient. However, the value ($V_{ri}$) also negatively correlates with the fraction (P(i)) in view of the fact that more commonly used ingredients are less likely to correspond to the main ingredients. Consideration of the fraction (P(i)) improves the accuracy of the determination of the main ingredients.

The main ingredients are determined according to the ingredients which have values ($V_{ri}$) equal to or greater than a threshold value. The threshold value may, for example, be an absolute threshold and/or correspond to a minimum/maximum number of main ingredients and/or correspond to a first drop in importance above a certain threshold, etc.

The controller may be configured to sequence the values ($V_{ri}$) calculated for each ingredient (i) by size, determine the largest difference between consecutive values in the sequence, and identify the pair of consecutive values in the sequence corresponding to the largest difference, wherein the threshold value is equal to the larger value of the pair.

By identifying the pair of consecutive values in the sequence having the largest difference between them, the method enables determination of the main ingredients. The main ingredients have values which are equal to or greater than the larger value of the pair having the largest difference between them. This larger value corresponds to the threshold value.

The controller may be configured to calculate the value ($V_{ri}$) from the mass fraction ($w_{ri}$) and the fraction (P(i)) using the following formula: $V_{ri}=-w_{ri} \log(P(i))$.

−log(P(i)) may be used to ensure that the value ($V_{ri}$) decreases with increasing fraction (P(i)), which reflects the fact more commonly used ingredients are less likely to correspond to the main ingredients. The value ($V_{ri}$) is the product of the mass fraction ($w_{ri}$) and −log(P(i)), which means that the value ($V_{ri}$) increases as the mass fraction ($w_{ri}$) of each ingredient (i) in the food recipe (r) increases. The product of mass fraction ($w_{ri}$) and the logarithmic function of the fraction (P(i)), in this case −log(P(i)), may be termed a "cross entropy form".

The controller may be configured to determine a parameter relating to the similarity of food recipes based on the determined main ingredients and/or based on determined non-main ingredients of the respective food recipes, wherein the determined non-main ingredients are the ingredients which are not the main ingredients of the respective food recipes.

The non-main ingredients may be regarded as a seasoning indicator, since seasonings tend to correspond to the ingredients excluded during identification of the main ingredients. The non-main ingredient identification may thus complement the main ingredient identification, such as to add or provide the alternative of recipe flavor similarity determination to main ingredient similarity determination.

The parameter (Sim($r_1$, $r_2$)) may be based on the determined main ingredients, and may be defined by the following formula:

$$\text{Sim}(r_1, r_2) = \frac{\sum_{j \text{ is main ingredient in } r_1 \text{ and } r_2} \min(w_{r_1 j}, w_{r_2 j}) \cdot \log(P(j))}{\sum_{j \text{ is main ingredient in } r_1 \text{ or } r_2} \max(w_{r_1 j}, w_{r_2 j}) \cdot \log(P(j))} \quad \text{(Formula 1)}$$

wherein $w_{r_1 j}$ and $w_{r_2 j}$ are the mass fractions of the main ingredient j in the respective recipes $r_1$ and $r_2$; P(j) is the fraction of said population which uses the main ingredient j.

The parameter (Sim($r_1$, $r_2$)) may alternatively be based on the determined non-main ingredients, and may be defined by the following formula:

$$\text{Sim}(r_1, r_2) = \frac{\sum_{k \text{ is non-main ingredient in } r_1 \text{ and } r_2} \min(w_{r_1 k}, w_{r_2 k}) \cdot \log(1 - P(k))}{\sum_{k \text{ is non-main ingredient in } r_1 \text{ or } r_2} \max(w_{r_1 k}, w_{r_2 k}) \cdot \log(1 - P(k))} \quad \text{(Formula 2)}$$

wherein $w_{r_1 k}$ an $w_{r_2 k}$ are the mass fractions of the non-main ingredient in the respective recipes $r_1$ and $r_2$; P(k) is the fraction of said population which uses the non-main ingredient k.

More generally, the above similarity parameter may not utilise the determined main ingredients or the determined non-main ingredients, but use the complete set of ingredients for both of the respective recipes. In other words, whilst there may be computational efficiency benefits to carrying out the similarity comparison using only the identified main ingredients or non-main ingredients, this may not be essential for the similarity assessment. Such a similarity comparison may use the identity of each ingredient of the respective recipes, the mass fraction of each ingredient of the respective recipes, and/or the respective fractions of the population of known recipes which use each ingredient of the respective recipes to determine the parameter. For example, the following formula, which does not require main ingredient determination, may be used:

$$\text{Sim}(r_1, r_2) = \frac{\sum_{i \text{ is in } r_1 \text{ and } r_2} \min(w_{r_1 i}, w_{r_2 i}) \cdot \log(P(i))}{\sum_{i \text{ is in } r_1 \text{ or } r_2} \max(w_{r_1 i}, w_{r_2 i}) \cdot \log(P(i))} \quad \text{(Formula 3)}$$

wherein, in Formula 3, $w_{r_1 i}$ and $w_{r_2 i}$ are the mass fractions of the ingredient i in the respective recipes $r_1$ and $r_2$. P(i) is the fraction of the population which uses the ingredient i, as noted above.

Using the ingredient data itself to compare recipes may provide a means of filtering recipes, e.g. for the purpose of providing a recommendation to a user, without relying on user endorsement data which is required in collaborative filtering techniques. This may be particularly advantageous for relatively large recipe databases which have numerous recipes to which no user feedback has been provided.

The controller may be configured to: use a word similarity model to determine a similarity score for each pairwise combination of the determined main ingredients or non-main ingredients of the respective recipes; use the similarity scores to identify pairs of main or non-main ingredients of the respective recipes; and use a threshold of the similarity score to identify any unpaired main or non-main ingredients of the respective recipes. The pairwise combination with the highest similarity score may, for example, be identified as a pair of main or non-main ingredients, as the case may be.

The parameter (Sim($r_1$, $r_2$)) may be based on the determined main ingredients, and may be defined by the following formula:

$$\text{Sim}(r_1, r_2) = \frac{\sum_{l,m \text{ are paired main ingredients}} \min(w_{r_1 l}, w_{r_2 m}) \cdot \log(P(l) \cdot P(m)) \cdot \text{Sim}(l, m)}{\sum_{l,m \text{ are paired main ingredients}} \max(w_{r_1 l}, w_{r_2 m}) \cdot \log(P(l) \cdot P(m)) + 2\sum_{n \text{ is unpaired main ingredient in } r_1 \text{ or } r_2} \max(w_{r_1 n}, w_{r_2 n}) \cdot \log(P(n))} \quad \text{(Formula 4)}$$

wherein $w_{r_1 l}$ is the mass fraction of main ingredient l, paired with m, in recipe $r_1$; $w_{r_2 m}$ is the mass fraction of main ingredient m, paired with l, in recipe $r_2$; P(l) is the fraction of said population which uses the ingredient l; P(m) is the fraction of said population which uses the ingredient m; Sim(l, m) is the similarity score for the paired main ingredients (l, m); $w_{r_1 n}$ and $w_{r_2 n}$ are the mass fractions of the unpaired main ingredient n in the respective recipes $r_1$ and $r_2$; P(n) is the fraction of said population which uses the unpaired main ingredient n.

If the ingredient similarity function takes Sim(l, m)=1 for l=m=j, and Sim(l, m)=0 for l≠m, Formula 4 will reduce to Formula 1.

The parameter (Sim($r_1$, $r_2$)) may alternatively be based on the determined non-main ingredients, and may be defined by the following formula:

$$\text{Sim}(r_1, r_2) = \quad \text{(Formula 5)}$$

$$\frac{\sum_{o,p \text{ are paired non-main ingredients}} \min(w_{r_1 o}, w_{r_2 p}) \cdot \log(P(l) \cdot P(m)) \cdot \text{Sim}(l, m)}{\sum_{o,p \text{ are paired non-main ingredients}} \max(w_{r_1 o}, w_{r_2 p}) \cdot \log((1 - P(o)) \cdot P(1 - (p))) + 2\sum_{q \text{ is unpaired non-main ingredient in } r_1 \text{ or } r_2} \max(w_{r_1 q}, w_{r_2 q}) \cdot \log(1 - P(q))}$$

wherein $w_{r_1 o}$ is the mass fraction of non-main ingredient o, paired with p, in recipe $r_1$; $w_{r_2 p}$ is the mass fraction of non-main ingredient p, paired with o, in recipe $r_2$; P(o) is the fraction of said population which uses the ingredient o; P(p) is the fraction of said population which uses the ingredient p; Sim(o, p) is the similarity score for the paired non-main ingredients (o, p); $w_{r_1 q}$ and $w_{r_2 q}$ are the mass fractions of the unpaired non-main ingredient q in the respective recipes $r_1$ and $r_2$; P(q) is the fraction of said population which uses the unpaired non-main ingredient q.

If the ingredient similarity function takes Sim(o, p)=1 for o=p=k, and Sim(o, p)=0 for o≠p, Formula 5 will reduce to Formula 2.

As noted above, the similarity parameter may not utilise the determined main ingredients or the determined non-main ingredients, but use the complete set of ingredients for both of the respective recipes. For example, the following formula, which does not require main ingredient identification, may be used:

$$\text{Sim}(r_1, r_2) = \quad \text{(Formula 6)}$$

$$\frac{\sum_{i,s \text{ are paired main ingredients}} \min(w_{r_1 i}, w_{r_2 s}) \cdot \log(P(i) \cdot P(s)) \cdot \text{Sim}(i, s)}{\sum_{i,s \text{ are paired ingredients}} \max(w_{r_1 i}, w_{r_2 m}) \cdot \log(P(i) \cdot P(s)) + 2\sum_{t \text{ is unpaired main ingredient in } r_1 \text{ or } r_2} \max(w_{r_1 t}, w_{r_2 t}) \cdot \log(P(t))}$$

wherein $w_{r_1 i}$ is the mass fraction of ingredient i, paired with s, in recipe $r_1$; $w_{r_2 s}$ is the mass fraction of ingredient s, paired with i, in recipe $r_2$; P(i) is the fraction of said population which uses the ingredient i; P(s) is the fraction of said population which uses the ingredient s; Sim(i,s) is the similarity score for the paired main ingredients (i, s); $w_{r_1 t}$ and $w_{r_2 t}$ are the mass fractions of the unpaired ingredient t in the respective recipes $r_1$ and $r_2$; P(t) is the fraction of said population which uses the unpaired ingredient t.

If the ingredient similarity function takes Sim(i, s)=1 for i=s, and Sim(i, s)=0 for i≠s, Formula 6 will reduce to Formula 3.

The system may comprise a user interface adapted to enable user entry of the identity and mass of each ingredient (i) in the food recipe (r), wherein the controller is configured to calculate the mass fraction ($w_{ri}$) of each ingredient (i) in the food recipe (r) from the mass of each ingredient (i) entered via the user interface. Any suitable user interface may be used for this purpose, e.g. a touchscreen.

The system may comprise a database of recipes, wherein the second input receives the identity of ingredients of each known recipe of the population of known recipes from the database. Suitable databases containing such recipe information are currently available. For example, one such database is the "NutriU" database from Philips.

According to another aspect there is provided a cooking appliance comprising a heating element, and the system as defined above, wherein the controller is configured to control the heating element based on the determined main ingredients.

The system as described above enables enhanced control over the cooking appliance owing to the greater accuracy in the main ingredients determination. The risk of the final dish being undercooked or overcooked may therefore be reduced.

The heating element may, for instance, be controlled using the masses of the determined main ingredients in the food recipe. This may enable precise control over the cooking parameters, in order to assist reducing of the risk of the final dish being undercooked or overcooked.

The controller may be configured to control the temperature of the heating element based on the determined main ingredients. Alternatively or additionally, the controller may be configured to control the duration of heating provided by the heating element based on the determined main ingredients.

The key selections in terms of the cooking parameters may be the temperature of the heating element and the duration of heating provided by the heating element. By making such selections on the basis of the main ingredients determined using the system described above, the cooking parameters may be more precisely tailored to the recipe, e.g. than if the main ingredients were determined solely on the basis of their respective mass fractions in the recipe.

According to still another aspect there is provided a computer implemented method for determining the main ingredients of a food recipe, the method comprising:

receiving the identity and mass fraction ($w_{ri}$) of each ingredient (i) in the food recipe (r);

receiving the identity of ingredients of each known recipe of a population of known recipes;

calculating, for each ingredient (i), the fraction (P(i)) of the population which uses the ingredient;

calculating, using the fraction (P(i)) and the mass fraction ($w_{ri}$), a value ($V_{ri}$) which positively correlates with the mass fraction ($w_{ri}$) and negatively correlates with the fraction (P(i)); and determining the main ingredients according to the ingredients which have values ($V_{ri}$) equal to or greater than a threshold value.

The method may further comprise: sequencing the values ($V_{ri}$) calculated for each ingredient by size; determining the largest difference between consecutive values in the sequence; and identifying the pair of consecutive values in the sequence corresponding to the largest difference, wherein the threshold value is equal to the larger value of the pair.

The calculating of the value ($V_{ri}$) from the mass fraction ($w_{ri}$) and the fraction (P(i)) may use the following formula: $V_{ri} = -w_{ri} \log(P(i))$.

The method may further comprise determining a parameter relating to the similarity of food recipes based on the determined main ingredients and/or based on determined non-main ingredients of the respective food recipes, wherein the determined non-main ingredients are the ingredients which are not the main ingredients of the respective food recipes.

The parameter (Sim($r_1$, $r_2$)) may be based on the determined main ingredients, and may be defined by the Formula 1 above. The parameter (Sim($r_1$,$r_2$)) may alternatively be based on the determined non-main ingredients, and may be defined by Formula 2 above.

As noted above, the above similarity parameter may not utilise the determined main ingredients or the determined non-main ingredients, but use the complete set of ingredients for both of the respective recipes. In other words, whilst there may be computational efficiency benefits to carrying out the similarity comparison using only the identified main ingredients or non-main ingredients, this may not be essential for the similarity assessment. Such a similarity comparison may use the identity of each ingredient of the respective recipes, the mass fraction of each ingredient of the respective recipes, and/or the respective fractions of the population of known recipes which use each ingredient of the respective recipes to determine the parameter. For example, the Formula 3 above may be used to determine the parameter.

Using the ingredient data itself to compare recipes may provide a means of filtering recipes, e.g. for the purpose of providing a recommendations to a user, without relying on user endorsement data which is required in collaborative filtering techniques. This may be particularly advantageous for relatively large recipe databases which have numerous recipes to which no user feedback has been provided.

The method may comprise: using a word similarity model to determine a similarity score for each pairwise combination of the determined main ingredients or non-main ingredients of the respective recipes; using the similarity scores to identify pairs of main or non-main ingredients of the respective recipes which are most similar; and using a threshold of the similarity score to identify any unpaired main or non-main ingredients of the respective recipes.

The parameter $(Sim(r_1, r_2))$ may be based on the determined main ingredients, and may be defined by the Formula 4 above.

The parameter $(Sim(r_1, r_2))$ may alternatively be based on the determined non-main ingredients, and may be defined by Formula 5 above.

As noted above, the similarity parameter may not utilise the determined main ingredients or the determined non-main ingredients, but use the complete set of ingredients for both of the respective recipes. For example, the above Formula 6, which does not require main ingredient identification, may be used According to a further aspect, there is provided a computer program which is adapted, when the program is run on a computer, to implement the method as defined above.

BRIEF DESCRIPTION OF THE DRAWINGS

Embodiments of the invention are described in more detail and by way of non-limiting examples with reference to the accompanying drawings, wherein.

DETAILED DESCRIPTION OF THE EMBODIMENTS

It should be understood that the detailed description and specific examples, while indicating exemplary embodiments of the apparatus, systems and methods, are intended for purposes of illustration only and are not intended to limit the scope of the invention. These and other features, aspects, and advantages of the apparatus, systems and methods of the present invention will become better understood from the following description, appended claims, and accompanying drawings. It should be understood that the Figures are merely schematic and are not drawn to scale. It should also be understood that the same reference numerals are used throughout the Figures to indicate the same or similar parts.

Provided is a system for determining the main ingredients of a food recipe. The system comprises a first input for receiving the identity and mass fraction $(w_{ri})$ of each ingredient (i) in the food recipe (r), and a second input for receiving the identity of ingredients of each known recipe of a population of known recipes. The system further includes a controller configured to calculate, for each ingredient (i), the fraction (P(i)) of the population which uses the ingredient. The controller then calculates, using the fraction (P(i)) and the mass fraction $(w_{ri})$, a value $(V_{ri})$ which positively correlates with the mass fraction $(w_{ri})$ and negatively correlates with the fraction (P(i)). The main ingredients are then determined according to the ingredients which have values $(V_{ri})$ equal to or greater than a threshold value.

The system enables more accurate determination of the main ingredients of a recipe, e.g. in comparison to a determination which only makes use of the mass percentages of the ingredients. This more accurate main ingredient determination, in turn, enables more precise tailoring of cooking parameters, such as the temperature at which food ingredients are cooked and the duration of cooking, to the recipe. Such superior tailoring of the cooking parameters to the recipe may reduce the risk of the final dish being undercooked or overcooked.

Moreover, determining the nutritional composition of the recipe may be based on the determined main ingredients, rather than on every single ingredient in the recipe, such as to save on computational resources. Since the system enables more accurate determination of the main ingredients, the nutritional composition calculation may be both efficient and accurate.

Further advantages are also envisaged. For example, when scaling up/down the cooking time according to the amounts of ingredients being different from those provided in a given recipe, the cooking time scaling rule depends on the food ingredients, and especially the main ingredients. Therefore, the main ingredient determination can be applied as a first step to enable more accurate and efficient scaling.

For instance, the doneness of the fried potato recipe in airfryer is evaluated by the weight loss, whereas the doneness of many other foodstuffs is determined by the core temperature. The scaling rules for fried potato recipes may therefore be quite different from those of recipes not including potato as a main ingredient. Therefore, the main ingredient determination may be applied in such a scenario as a first step to evaluate whether the recipe should be regarded as a fried potato recipe, i.e. having potato as a main ingredient, or not.

The similarity between two different recipes can also be evaluated in an efficient and accurate manner by comparing the main ingredients determined for the respective recipes, as will be described in more detail herein below.

Figure 1:
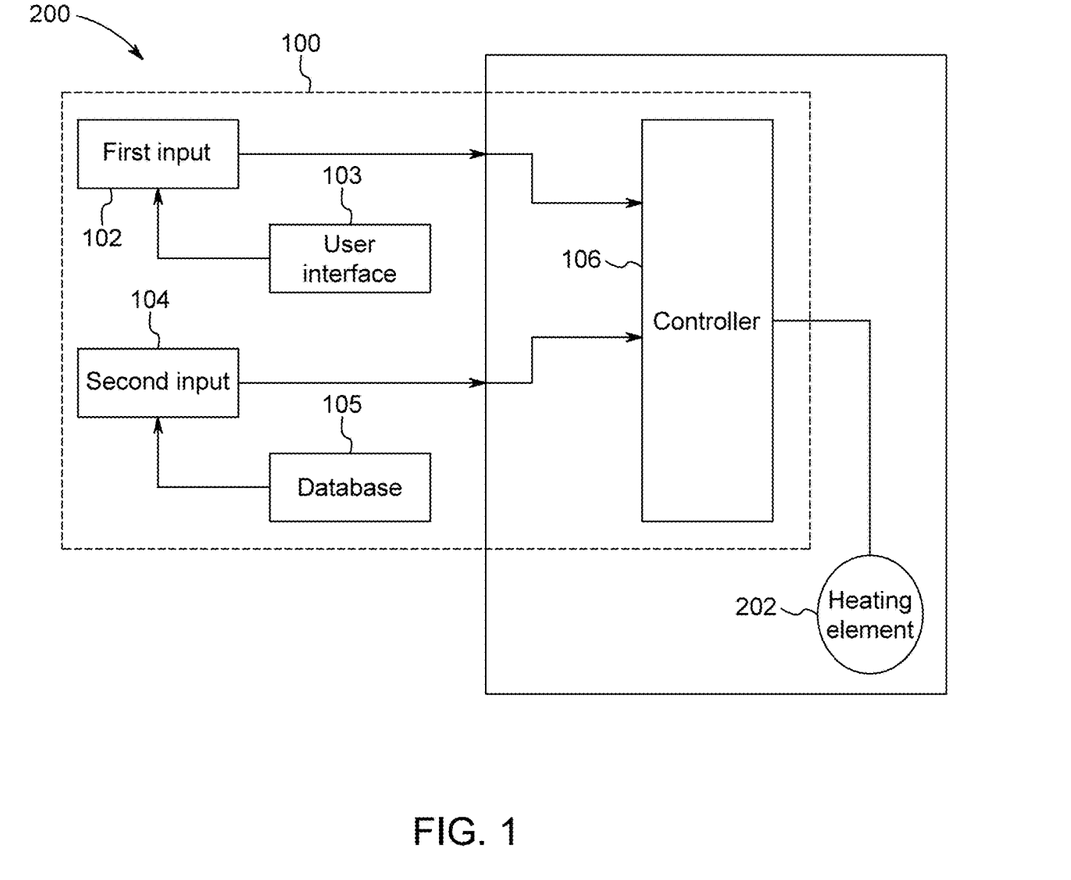
FIG. 1 shows a cooking appliance having a system according to an embodiment.

FIG. 1 shows a system 100 according to an embodiment. The system 100 is part of a cooking appliance 200 having a heating element 202 which is controlled by the controller 106. The cooking appliance 200 may be, for instance, an oven, an air fryer, an electric hob, etc. Any suitable heating element 202 may be contemplated, such as a resistive heating element.

The controller 106 controls the heating element 106 based on the determined main ingredients. In this respect, the controller 106 may control the temperature of the heating element 202 on the basis of the determined main ingredients. Alternatively or additionally, the controller 106 may be configured to control the duration of heating provided by the heating element 202 based on the determined main ingredients. The heating element 202 may also be controlled by the controller 106 on the basis of the masses, and optionally the mass factions ($w_{r,i}$), of the determined main ingredients in the food recipe. The arrow between the controller 106 and the heating element 202 is intended to represent the control signals passing from the controller 106 to the heating element 202.

By controlling the heating element 202 of the cooking appliance 200 on the basis of the accurate determination of the main ingredients provided by the system 100, precise control over the cooking parameters may be enabled, in order to assist reducing of the risk of the final dish being undercooked or overcooked.

At this point it is noted that although the system 100 is employed in a cooking appliance 200 in FIG. 1, this is for illustrative purposes only, and should not be regarded as limiting the applicability of the system 100. In this respect, the system 100 may be used independently of a cooking appliance 200, e.g. for purposes other than controlling the cooking appliance 200. In other words, the output, in the form of the determined main ingredients, provided by the system 100 may be employed in other ways aside from being used in controlling the heating element 202 of a cooking appliance 200.

For example, the system 100 may be employed to extract the main ingredients of a food recipe for the purpose of determining the nutritional composition of the food recipe. Basing such a nutritional composition calculation on the determined main ingredients, rather than the entire list of ingredients, saves on computational resources. Moreover, the system 100 enables more accurate determination of the main ingredients than, for instance, a determination which is solely based on the mass fractions of the ingredients in the food recipe, as previously described. Accordingly, in such an example, the main ingredient determination by the system 100 enables efficient and accurate determination of the nutritional composition.

As shown in FIG. 1, the system 100 has a first input 102 which is for receiving the identity and mass fraction ($w_{r,i}$) of each ingredient (i) in the food recipe (r). As shown in FIG. 1, the system 100 may comprise a user interface 103 adapted to enable user entry of the identity and mass of each ingredient (i) in the food recipe (r). The arrow between the user interface 103 and the first input 102 is intended to represent the information being received by the first input 102 from the user interface 103. Any suitable user interface may be used for this purpose, e.g. a touchscreen.

The mass of each ingredient (i) may be converted to a mass fraction ($w_{r,i}$) in the food recipe (r). This conversion may, for example, be carried out by the controller 106, and subsequently received by the first input 102. This may be more convenient for the user because typical recipes list the absolute quantities of each food ingredient. In order to effect this conversion, the controller may convert different measurement systems, e.g. volumes, "cups", "tablespoons", and imperial measurements and so on, into a single, e.g. metric, measurement of the mass of each food ingredient (i). Where the quantity is a volume, the density of the food ingredient is used to determine its mass. In this respect, the system 100 may, for instance, have a memory which stores densities of food ingredients and/or enables the user to enter an estimate for the density via the user interface 103, and so on. Once the masses of each ingredient (i) are known, the mass fractions for each ingredient (i) can then be calculated by dividing the mass of each ingredient by the total mass of the ingredients, as will readily be appreciated by the skilled person.

Alternatively, the user may enter the mass fraction ($w_{r,i}$), rather than the mass, of each ingredient (i) in the food recipe (r), e.g. if this information is already available.

In any case, the mass fraction ($w_{r,i}$) information, together with the identity of each food ingredient (i) in the food recipe (r) is received by the first input 102.

Further evident in FIG. 1 is the second input 104 which receives the identity of ingredients of each known recipe of a population of known recipes. The system may comprise a database 105 of recipes, and the second input 104 receives the identity of ingredients of each known recipe of the population of known recipes from the database 105. The information corresponding to the population of known recipes being received by the second input 104 is represented in FIG. 1 by the arrow between the database 105 and the second input 104. Suitable databases containing such recipe information are currently available. For example, one such database is the "NutriU" database from Philips. The "NutriU" database is a recipe information backend, which is intended to serve all Philips kitchen appliance products and improve user experience. Rather than merely presenting various recipes on this backend, the recipe data may be employed, e.g. in conjunction with the system 100, to provide recipe nutrition calculation, recipe similarity comparison, recipe conversion between different product models, and even automatic recipe generation.

In practice, food ingredients may have more than one term which is used to identify them. The system 100 may take account of such synonyms, for example, by the database 105 also storing such synonym information. Tools for recognizing synonyms are well-known per se and will not be further described herein for the sake of brevity only.

As represented by the arrows between the first input 102 and the controller 106, and between the second input 104 and the controller 106, the controller 106 makes use of the information respectively provided by the first input 102 and the second input 104. In this respect, the controller 106 is configured to calculate, for each ingredient (i), the fraction (P(i)) of the population which uses the ingredient. This fraction (P(i)) may be expressed by the following formula:

$$P(i) = \frac{\#\ \{r\ |\ i\ \text{in recipe}\ r\}}{\#\ \text{all recipes}} \quad \text{(Formula A)}$$

all recipes is the number of occurrences of ingredient i in the population of known recipes. This fraction, or probability, (P(i)) reflects the importance of an ingredient in general.

The higher the frequency of an ingredient among all the known recipes included in the population, the less important it is, i.e. the less likely it is to correspond to a main ingredient. Many seasonings and condiments, which are commonly included in recipes, would correspond to a relatively high fraction (P(i)).

The controller 106 then calculates, using the fraction (P(i)) and the mass fraction ($w_{r,i}$) which is provided by the first input 102, a value ($V_{ri}$) which positively correlates with the mass fraction ($w_{ri}$) and negatively correlates with the fraction (P(i)).

For each ingredient (i), the mass fraction ($w_{ri}$) and the fraction (P(i)) of the population will both be greater than 0 but less than 1. The value ($V_{ri}$) positively correlates with the mass fraction in view of the fact that, to a first approximation, a greater mass fraction ($w_{ri}$) of an ingredient in a recipe will tend to increase the likelihood of that ingredient corresponding to a main ingredient. However, the value ($V_{ri}$) also negatively correlates with the fraction (P(i)) in view of the fact that more commonly used ingredients are less likely to correspond to the main ingredients. Consideration of the fraction (P(i)) improves the accuracy of the determination of the main ingredients in comparison to when the mass fraction of each ingredient is the sole parameter which is taken into account.

Any suitable means of calculating the value ($V_{ri}$) may be contemplated, providing the value ($V_{ri}$) positively correlates with the mass fraction ($w_{ri}$) and negatively correlates with the fraction (P(i)), as previously described.

In an embodiment, the controller 106 is configured to calculate the value ($V_{ri}$) from the mass fraction ($w_{ri}$) and the fraction (P(i)) using the following formula: $V_{ri} = -w_{ri} \log(P(i))$ (Formula B). Here, $w_{ri} = 0$ may means that ingredient (i) is not in the recipe (r).

$-\log(P(i))$ may be used to ensure that the value ($V_{ri}$) decreases with increasing fraction (P(i)), which reflects the fact more commonly used ingredients are less likely to correspond to the main ingredients. The value ($V_{ri}$) is the product of the mass fraction ($w_{ri}$) and $-\log(P(i))$, which means that the value ($V_{ri}$) increases as the mass fraction ($w_{ri}$) of each ingredient (i) in the food recipe (r) increases. The product of mass fraction ($w_{ri}$) and the logarithmic function of the fraction (P(i)), in this case $-\log(P(i))$, may be termed a "cross entropy form".

$-w_{ri} \log(P(i))$ has been found to be a reasonable metric to evaluate the importance of an ingredient. This metric incorporates ingredient information in general (via the $-\log (P(i))$ term) as well as in specific recipe (via the $w_{ri}$ term), and results in a cross entropy form. This metric can help to determine the main ingredients in a recipe with a convincing criterion.

The main ingredients are determined according to the ingredients which have values ($V_{ri}$) equal to or greater than a threshold value. Any suitable means for determining the threshold value may be used. The threshold value may, for example, be an absolute threshold and/or correspond to a minimum/maximum number of main ingredients and/or correspond to a first drop in importance above a certain threshold, etc.

The system 100 thus evaluates the importance of an ingredient in a given recipe. This value ($V_{ri}$) index accounts for both the statistical information of ingredients in all existing recipes and the mass fraction of each ingredient in the recipe and thus trims inessential ingredients and keeps, i.e. determines, the main ingredients.

In an embodiment, the controller 106 sequences the values ($V_{ri}$) calculated for each ingredient in the food recipe in order by size. For example, the ingredients i in recipe r may be sorted in descending order of $V_{ri}$, i.e. $V_{ri_1} \geq V_{ri_2} \geq \ldots \geq V_{ri_n} \geq V_{ri_{n+1}} \geq \ldots$ . The controller 106 may be configured to determine the largest difference between consecutive values in the sequence, and identify the pair of consecutive values in the sequence corresponding to the largest difference. The threshold value is equal to the larger value of the pair. This process may be regarded as finding k such that $$V_{ri_k} - V_{ri_{k+1}} = \max_n\{V_{ri_n} - V_{ri_{n+1}}\}.$$

Figure 2:
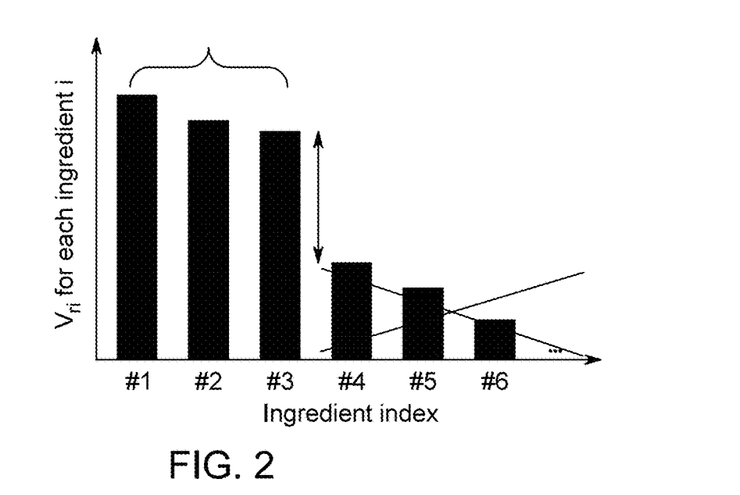
FIG. 2 shows a bar chart of ingredients in a given food recipe and their respective values $(V_{ri})$.

FIG. 2 shows food ingredients ranked by their values ($V_{ri}$) in descending order. FIG. 2 provides an intuitive visualization of the inessential ingredient trimming procedure or, expressed the other way around, the main ingredients determination procedure. The ingredients are sorted in descending order of value ($V_{ri}$). As shown in FIG. 2, the largest decrease in value ($V_{ri}$) (see the double-headed arrow in FIG. 2) in the sequence is that between ingredients #3 and #4. Accordingly, the threshold value is equal to the value ($V_{ri}$) for ingredient #3. Ingredients #1, #2 and #3 are thus determined as the main ingredients. Ingredients #4, #5 and #6 have values which are less than the threshold value, and therefore do not correspond to the main ingredients. This is illustrated by the lines scoring out ingredients #4, #5 and #6 in FIG. 2.

Figure 3:
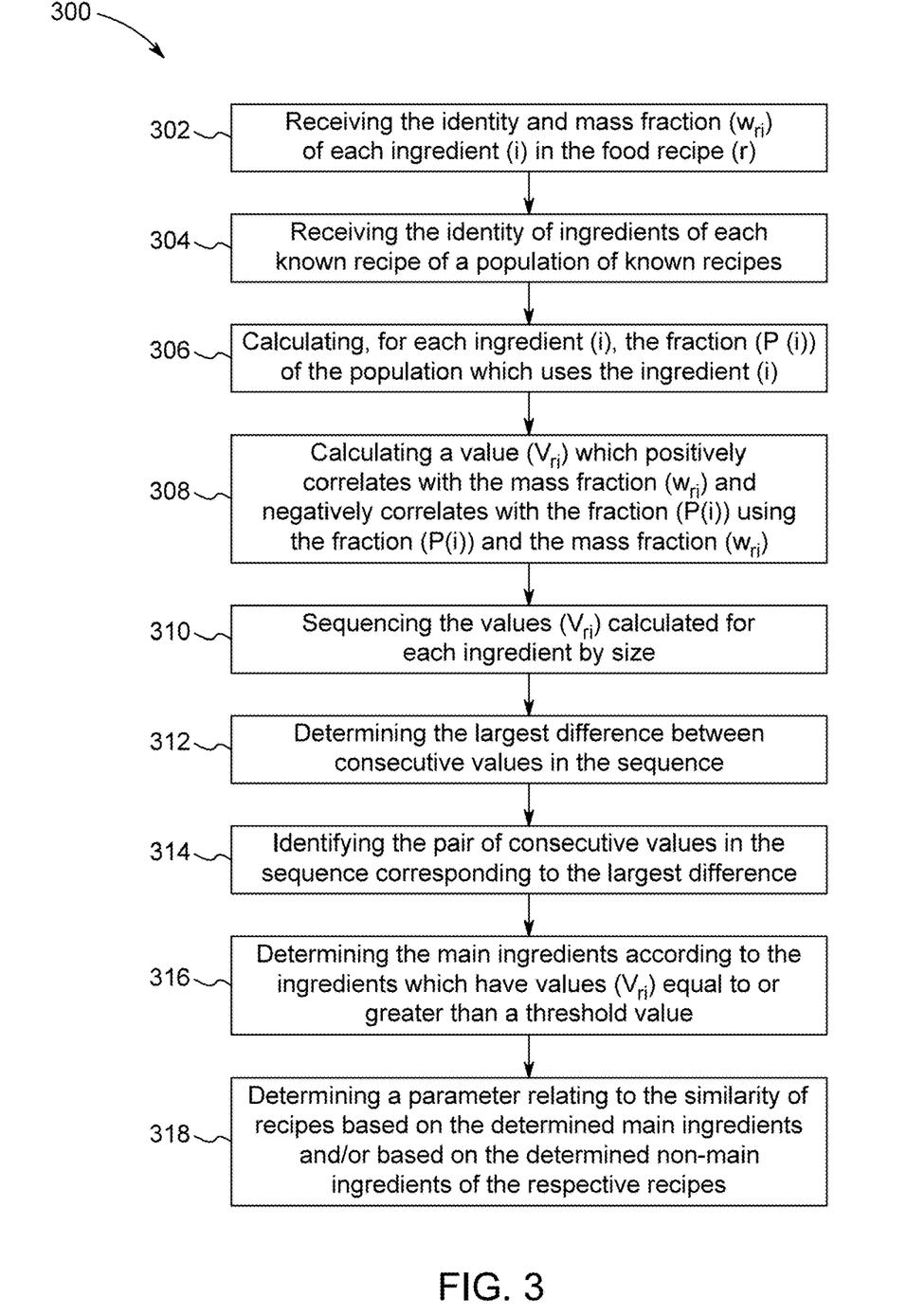
FIG. 3 shows a flowchart of a method according to an embodiment.

FIG. 3 shows a flowchart of a computer implemented method 300 according to an embodiment. In step 302, the identity and mass fraction ($w_{ri}$) of each ingredient (i) in the food recipe (r) are received. The identity of ingredients of each known recipe of a population of known recipes is received in step 304.

In step 306, the fraction (P(i)) of the population which uses the ingredient is calculated for each ingredient (i). The fraction (P(i)) and the mass fraction ($w_{ri}$) are then used in step 308 to calculate a value ($V_{ri}$) which positively correlates with the mass fraction ($w_{ri}$) and negatively correlates with the fraction (P(i)). The main ingredients are determined in step 316 according to the ingredients which have values ($V_{ri}$) equal to or greater than a threshold value.

In an embodiment, the method 300 further comprises sequencing 310 the values ($V_{ri}$) calculated for each ingredient by size. In step 312, the largest difference between consecutive values in the sequence is determined. The pair of consecutive values in the sequence corresponding to the largest difference is identified in step 314. The threshold value referred to in step 316 is equal to the larger value of the pair, as previously described.

The method 300 may further comprise the step 318 of determining a parameter relating to the similarity of recipes based on the determined main ingredients and/or based on the determined non-main ingredients of the respective recipes.

The non-main ingredients may be regarded as a seasoning indicator, since seasonings tend to correspond to the ingredients excluded during identification of the main ingredients. The non-main ingredient identification may thus complement the main ingredient identification, such as to add or provide the alternative of recipe flavor similarity determination to main ingredient similarity determination.

Step 318 may, for instance, be carried out via the controller 106 of the system 100 described above. On the basis of the degree of similarity between the recipes, as quantified by the parameter, the cooking parameter(s) already selected for one recipe may then be applied to other recipes for which the cooking parameters have not yet been selected. Cooking parameters may thus be selected more efficiently, i.e. using less computational capacity, than in the case where cooking parameters are selected based on the determined main ingredients ab initio.

The parameter (Sim($r_1$, $r_2$)) may be based on the determined main ingredients, and may be defined by the following formula:

$$\text{Sim}(r_1, r_2) = \frac{\sum_{k \text{ is non-main ingredient in } r_1 \text{ or } r_2} \min(w_{r_1 j}, w_{r_2 j}) \cdot \log(P(j))}{\sum_{k \text{ is non-main ingredient in } r_1 \text{ or } r_2} \max(w_{r_1 j}, w_{r_2 j}) \cdot \log(P(j))} \quad \text{(Formula 1)}$$

wherein $w_{r_1 j}$ and $w_{r_2 j}$ are the mass fractions of the main ingredient j in the respective recipes $r_1$ and $r_2$; P(j) is the fraction of said population which uses the main ingredient j.

The parameter (Sim($r_1$, $r_2$)) may alternatively be based on the determined non-main ingredients, and may be defined by the following formula:

$$\text{Sim}(r_1, r_2) = \frac{\sum_{k \text{ is non-main ingredient in } r_1 \text{ or } r_2} \min(w_{r_1 k}, w_{r_2 k}) \cdot \log(1 - P(k))}{\sum_{k \text{ is non-main ingredient in } r_1 \text{ or } r_2} \max(w_{r_1 k}, w_{r_2 k}) \cdot \log(1 - P(k))} \quad \text{(Formula 2)}$$

wherein $w_{r_1 k}$ and $w_{r_2 k}$ are the mass fractions of the non-main ingredient k in the respective recipes $r_1$ and $r_2$; P(k) is the fraction of said population which uses the non-main ingredient k.

More generally, the above similarity parameter may not utilise the determined main ingredients or the determined non-main ingredients, but use the complete set of ingredients for both of the respective recipes. In other words, whilst there may be computational efficiency benefits to carrying out the similarity comparison using only the identified main ingredients or non-main ingredients, this may not be essential for the similarity assessment. Such a similarity comparison may use the identity of each ingredient of the respective recipes, the mass fraction of each ingredient of the respective recipes, and/or the respective fractions of the population of known recipes which use each ingredient of the respective recipes to determine the parameter. For example, the following formula, which does not require main ingredient determination, may be used:

$$\text{Sim}(r_1, r_2) = \frac{\sum_{i \text{ is in } r_1 \text{ or } r_2} \min(w_{r_1 i}, w_{r_2 i}) \cdot \log(P(i))}{\sum_{i \text{ is in } r_1 \text{ or } r_2} \max(w_{r_1 i}, w_{r_2 i}) \cdot \log(P(i))} \quad \text{(Formula 3)}$$

wherein, in Formula 3, $w_{r_1 i}$ and $w_{r_2 i}$ are the mass fractions of the ingredient i in the respective recipes $r_1$ and $r_2$. P(i) is the fraction of the population which uses the ingredient i, as noted above.

Using the ingredient data itself to compare recipes may provide a means of filtering recipes, e.g. for the purpose of providing a recommendation to a user, without relying on user endorsement data which is required in collaborative filtering techniques. This may be particularly advantageous for relatively large recipe databases which have numerous recipes to which no user feedback has been provided.

The similarity determination step 318 may comprise using a word similarity model to determine a similarity score for each pairwise combination of the determined main ingredients or non-main ingredients of the respective recipes.

Ingredient names, especially in recipes from various sources, are not always well normalized. For instance, "seaweed" and "kelp" are almost the same ingredient but this fact may be problematic for a computer to recognize. Setting hard coded rules may not provide a durable or scalable solution especially when the number of recipes and ingredients expands. For this reason, a word embedding model, e.g. in the form of a deep learning model, may be used account for different ingredient terminology. Currently, well-trained and pre-trained models are known, such as the Word2Vec model by GOOGLE. Such models may be used directly. Such use may also have the effect of continuing to train the model by feeding recipe text into the model, such that the model gains specialised training in recipe terminologies.

Ingredient similarity (Sim(i, s)) may, for example, be evaluated by the cosine value of word vectors representing two ingredients i and s. Using this ingredient similarity score, the most similar ingredients may be paired prior to the next step of the calculation. The ingredient similarity score of each pairwise combination of the ingredients from two respective recipes may be calculated (step (i)). The most similar pairs, e.g. with the highest ingredient similarity score, may be identified as paired ingredients, and these paired ingredients are then excluded in subsequent comparison steps (step (ii)). Steps (ii) and (iii) may then be repeated until no further paired ingredients can be identified, e.g. using a threshold of the similarity score, which threshold distinguishes paired ingredients (i, s) from any unpaired ingredients (t). The similarity scores of the paired ingredients from the respective recipes may then be used in determination of the parameter relating to the similarity of recipes.

As noted above, the similarity parameter may, for example, use the complete set of ingredients for both of the respective recipes. For example, the following formula, which does not require main ingredient identification, may be used:

$$\text{Sim}(r_1, r_2) = \frac{\sum_{i,s \text{ are paired main ingredients}} \min(w_{r_1 i}, w_{r_2 s}) \cdot \log(P(i) \cdot P(s)) \cdot \text{Sim}(i, s)}{\sum_{i,s \text{ are paired ingredients}} \max(w_{r_1 i}, w_{r_2 m}) \cdot \log(P(i) \cdot P(s)) + 2\sum_{t \text{ is unpaired main ingredient in } r_1 \text{ or } r_2} \max(w_{r_1 t}, w_{r_2 t}) \cdot \log(P(t))} \quad \text{(Formula 6)}$$

wherein $w_{r_1 i}$ is the mass fraction of ingredient i, paired with s, in recipe $r_1$; $w_{r_2 s}$ is the mass fraction of ingredient s, paired with i, in recipe $r_2$; P(i) is the fraction of said population which uses the ingredient i; P(s) is the fraction of said population which uses the ingredient s; Sim(i,s) is the similarity score for the paired main ingredients (i, s); $w_{r_1 t}$ and $w_{r_2 t}$ are the mass fractions of the unpaired ingredient t in the respective recipes $r_1$ and $r_2$; P(t) is the fraction of said population which uses the unpaired ingredient t.

Note that for an unpaired ingredient "n" in recipe $r_1$ or $r_2$, either $w_{r_1 n}=0$ or $w_{r_2 n}=0$, so $\max(w_{r_1 n}, w_{r_2 n})$ just selects the nonzero one between them and contributes to the recipe dissimilarity which shows up in the denominator of the fraction.

If the ingredient similarity function takes Sim(i, s)=1 for i=s, and Sim(i, s)=0 for i≠s, Formula 6 will reduce to Formula 3.

The parameter (Sim($r_1,r_2$)) may alternatively be based on the determined main ingredients, which may benefit from less computational resources being required. The parameter (Sim($r_1, r_2$)) may, for instance, be defined by the following formula:

$$\text{Sim}(r_1, r_2) = \frac{\sum_{l,m \text{ are paired main ingredients}} \min(w_{r_1 l}, w_{r_2 m}) \cdot \log(P(l) \cdot P(m)) \cdot \text{Sim}(l, m)}{\sum_{l,m \text{ are paired main ingredients}} \max(w_{r_1 l}, w_{r_2 m}) \cdot \log(P(l) \cdot P(m)) + 2\sum_{n \text{ is unpaired main ingredient in } r_1 \text{ or } r_2} \max(w_{r_1 n}, w_{r_2 n}) \cdot \log(P(n))}$$

(Formula 4)

wherein $w_{r_1 l}$ is the mass fraction of main ingredient l, paired with m, in recipe $r_1$; $w_{r_2 m}$ is the mass fraction of main ingredient m, paired with l, in recipe $r_2$; P(l) is the fraction of said population which uses the ingredient l; P(m) is the fraction of said population which uses the ingredient m; Sim(l, m) is the similarity score for the paired main ingredients (l, m); $w_{r_1 n}$ and $w_{r_2 n}$ are the mass fractions of the unpaired main ingredient n in the respective recipes $r_1$ and $r_2$; P(n) is the fraction of said population which uses the unpaired main ingredient n.

If the ingredient similarity function takes Sim(l, m)=1 for l=m=j, and Sim(l, m)=0 for l≠m, Formula 4 will reduce to Formula 1.

In an alternative example, the parameter (Sim($r_1,r_2$)) may be based on the determined non-main ingredients, and may be defined by the following formula:

$$\text{Sim}(r_1, r_2) = \frac{\sum_{o,p \text{ are paired non-main ingredients}} \min(w_{r_1 o}, w_{r_2 p}) \cdot \log(P(l) \cdot P(m)) \cdot \text{Sim}(l, m)}{\sum_{o,p \text{ are paired non-main ingredients}} \max(w_{r_1 o}, w_{r_2 p}) \cdot \log((1 - P(o)) \cdot P(1 - (p))) + 2\sum_{q \text{ is unpaired non-main ingredient in } r_1 \text{ or } r_2} \max(w_{r_1 q}, w_{r_2 q}) \cdot \log(1 - P(q))}$$

(Formula 5)

wherein $w_{r_1 o}$ is the mass fraction of non-main ingredient o, paired with p, in recipe $r_1$; $w_{r_2 p}$ is the mass fraction of non-main ingredient p, paired with o, in recipe $r_2$; P(o) is the fraction of said population which uses the ingredient o; P (p) is the fraction of said population which uses the ingredient p; Sim(o, p) is the similarity score for the paired non-main ingredients (o, p); $w_{r_1 q}$ and $w_{r_2 q}$ are the mass fractions of the unpaired non-main ingredient q in the respective recipes $r_1$ and $r_2$; P(q) is the fraction of said population which uses the unpaired non-main ingredient q.

If the ingredient similarity function takes Sim(o, p)=1 for o=p=k, and Sim(o, p)=0 for o≠p, Formula 5 will reduce to Formula 2.

The above-described recipe similarity comparison may be applied to alleviate the problem of recipe recommendation cold start with limited user information. From very few trials of one specific user, the system or method according to some embodiments may reasonably recommend similar recipes using ingredients data, in particular main or non-main ingredients data. Nutritional value or flavor descriptors may also be utilised in the method or system based on such ingredients data. The recipe recommendation may thus be based on the intrinsic ingredient similarity, rather than on user preference at the population level. Such systems and methods may be a key enabler for many recipe backend applications, e.g., recipe recommendation, meal planner, and recipe data administration.

Similar recipes in terms of nutritional value may be recommended through recipe similarity index based on main ingredients, as previously described.

The recipe similarity parameters may be used combinatorially. The manner in which the combinations are made may also be customized by each user's personal preference.

The similarity evaluation may be employed for, for example, removing duplicate recipes from a database. Highly similar recipe pairs, for example, with a relatively high parameter (Sim($r_1,r_2$)), e.g. which reaches a duplicate identification threshold, may be identified. Such information may, for example, be outputted by the system to a food expert or nutritionist for final determination of whether the pair is a pair of duplicate recipes.

A further application may be recipe clustering and classification. The similarity assessment may, for instance, be used to monitor the diversity, quality of the recipes, especially those created by the users. Moreover, ingredient name unification, mapping, and hierarchical clustering may be enabled by using the previously described ingredient similarity scoring method.

Figure 4:
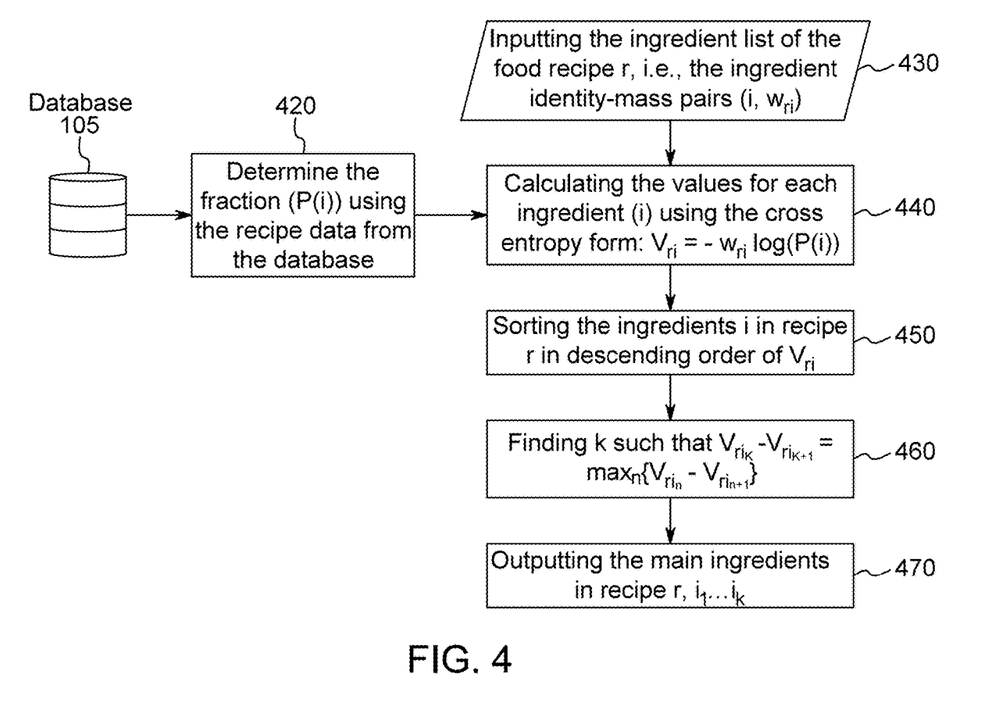
FIG. 4 shows a block diagram for illustrating a function of the system according to an embodiment.

FIG. 4 shows a block diagram for illustrating a function of a system according to an embodiment. Recipe data from the database 105 is used to determine the fraction (P(i)) in block 420. In block 430, the ingredient list of the food recipe r, i.e., the ingredient identity-mass pairs (i, $w_{ri}$) are inputted. The values for each ingredient (i) are calculated in block 440 using the above-described cross entropy form: $V_{ri}$=−$w_{ri}$ log(P(i)). In block 450, the ingredients i in recipe r are sorted in descending order of $V_{ri}$, i.e. $V_{ri_1} \geq V_{ri_2} \geq \ldots \geq V_{ri_n} \geq V_{ri_{n+1}} \geq \ldots$.

Block 460 corresponds to the step of finding k such that $$V_{ri_k} - V_{ri_{k+1}} = \max_n \{V_{ri_n} - V_{ri_{n+1}}\}.$$

In block 170, the main ingredients in recipe r, $i_1, \ldots, i_k$, are outputted.

Figure 5:
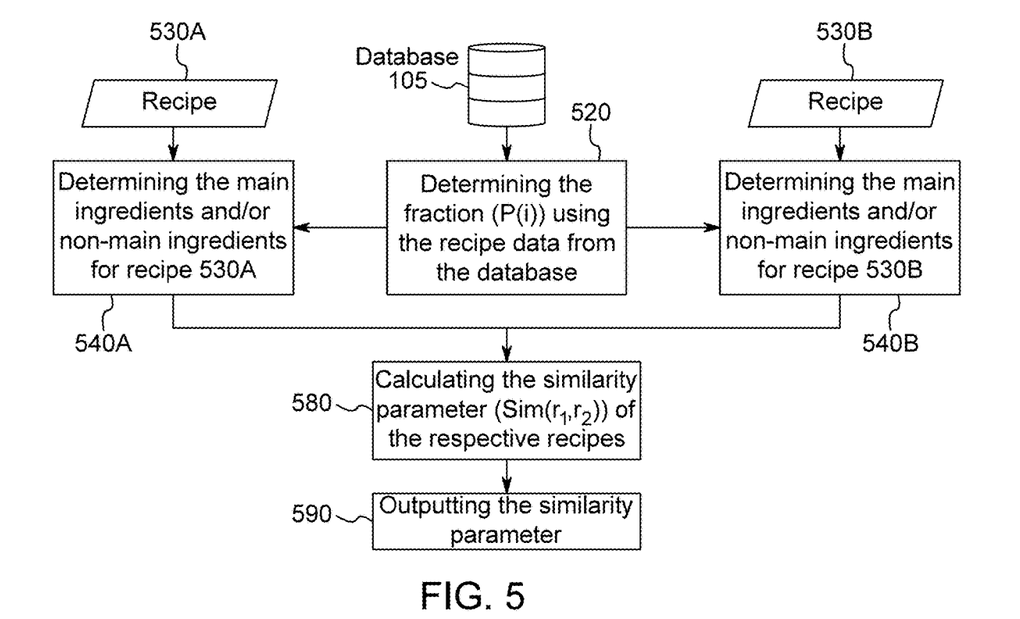
FIG. 5 shows a block diagram for illustrating a further function of the system according to another embodiment.

FIG. 5 shows block diagram for illustrating a further function of a system according to another embodiments. In this case, the system is for determining the similarity parameter (Sim($r_1,r_2$)). Recipe data from the database 105 is used to determine the fraction (P(i)) in block 520. In blocks 540A and 540B, the main ingredients and/or the non-main ingredients for the respective recipes 530A and 530B are determined. In block 580, the similarity parameter of the respective recipes is calculated (Sim($r_1, r_2$)). This parameter may involve calculation in various manners, e.g. using various ingredient indicators, ingredient similarity scoring, as previously described. In block 590, the similarity parameter is outputted.

Figure 6:
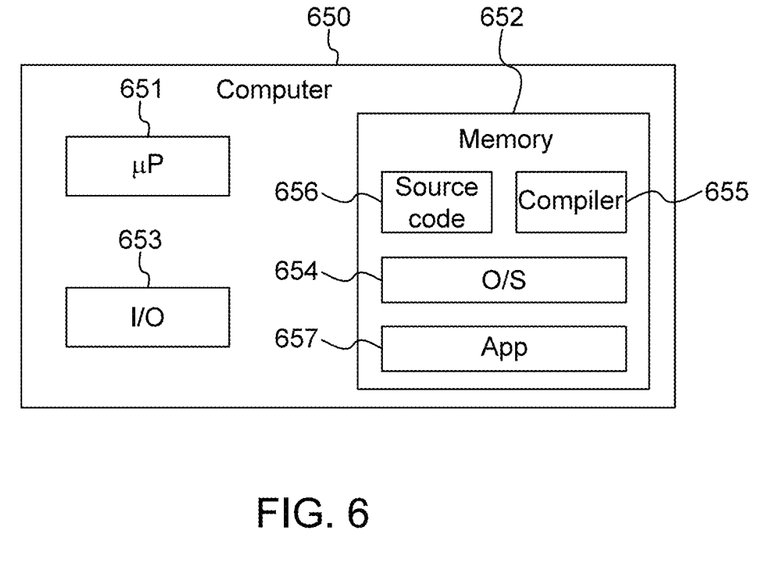
FIG. 6 shows a general computer architecture suitable for implementing the controller used in the system.

FIG. 6 illustrates an example of a computer 650 for implementing the controller described above. The computer 650 includes, but is not limited to, PCs, workstations, laptops, PDAs, palm devices, servers, storages, and the like. Generally, in terms of hardware architecture, the computer 650 may include one or more processors 651, memory 652, and one or more I/O devices 653 that are communicatively coupled via a local interface (not shown). The local interface can be, for example but not limited to, one or more buses or other wired or wireless connections, as is known in the art. The local interface may have additional elements, such as controllers, buffers (caches), drivers, repeaters, and receivers, to enable communications. Further, the local interface may include address, control, and/or data connections to enable appropriate communications among the aforementioned components.

The processor 651 is a hardware device for executing software that can be stored in the memory 652. The processor 651 can be virtually any custom made or commercially available processor, a central processing unit (CPU), a digital signal processor (DSP), or an auxiliary processor among several processors associated with the computer 650, and the processor 651 may be a semiconductor based microprocessor (in the form of a microchip) or a microprocessor.

The memory 652 can include any one or combination of volatile memory elements (e.g., random access memory (RAM), such as dynamic random access memory (DRAM), static random access memory (SRAM), etc.) and non-volatile memory elements (e.g., ROM, erasable programmable read only memory (EPROM), electronically erasable programmable read only memory (EEPROM), programmable read only memory (PROM), tape, compact disc read only memory (CD-ROM), disk, diskette, cartridge, cassette or the like, etc.). Moreover, the memory 652 may incorporate electronic, magnetic, optical, and/or other types of storage media. Note that the memory 652 can have a distributed architecture, where various components are situated remote from one another, but can be accessed by the processor 651.

The software in the memory 652 may include one or more separate programs, each of which comprises an ordered listing of executable instructions for implementing logical functions. The software in the memory 652 includes a suitable operating system (O/S) 654, compiler 655, source code 656, and one or more applications 657 in accordance with exemplary embodiments.

The application 657 comprises numerous functional components such as computational units, logic, functional units, processes, operations, virtual entities, and/or modules.

The operating system 654 controls the execution of computer programs, and provides scheduling, input-output control, file and data management, memory management, and communication control and related services.

Application 657 may be a source program, executable program (object code), script, or any other entity comprising a set of instructions to be performed. When a source program, then the program is usually translated via a compiler (such as the compiler 655), assembler, interpreter, or the like, which may or may not be included within the memory 652, so as to operate properly in connection with the operating system 654. Furthermore, the application 657 can be written as an object oriented programming language, which has classes of data and methods, or a procedure programming language, which has routines, subroutines, and/or functions, for example but not limited to, C, C++, C#, Pascal, BASIC, API calls, HTML, XHTML, XML, ASP scripts, JavaScript, FORTRAN, COBOL, Perl, Java, ADA, .NET, and the like.

The I/O devices 653 may include input devices such as, for example but not limited to, a mouse, keyboard, scanner, microphone, camera, etc. Furthermore, the I/O devices 653 may also include output devices, for example but not limited to a printer, display, etc. Finally, the I/O devices 653 may further include devices that communicate both inputs and outputs, for instance but not limited to, a network interface controller (NIC) or modulator/demodulator (for accessing remote devices, other files, devices, systems, or a network), a radio frequency (RF) or other transceiver, a telephonic interface, a bridge, a router, etc. The I/O devices 653 also include components for communicating over various networks, such as the Internet or intranet.

When the computer 650 is in operation, the processor 651 is configured to execute software stored within the memory 652, to communicate data to and from the memory 652, and to generally control operations of the computer 650 pursuant to the software. The application 657 and the operating system 654 are read, in whole or in part, by the processor 651, perhaps buffered within the processor 651, and then executed.

When the application 657 is implemented in software it should be noted that the application 657 can be stored on virtually any computer readable medium for use by or in connection with any computer related system or method. In the context of this document, a computer readable medium may be an electronic, magnetic, optical, or other physical device or means that can contain or store a computer program for use by or in connection with a computer related system or method.

Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. The mere fact that certain measures are recited in mutually different dependent claims does not indicate that a combination of these measures cannot be used to advantage. Any reference signs in the claims should not be construed as limiting the scope.

The invention claimed is:

1. A system for determining main ingredients of a food recipe, the system comprising:
    a first input for receiving, via a user interface, an identity and mass fraction ($w_{ri}$) of each ingredient in the food recipe;
    a second input for receiving, from a database, the identity of ingredients of each known food recipe of a population of known food recipes; and
    a controller configured to:
        calculate, for the each ingredient, fraction (P(i)) of said population of known food recipes which uses the ingredient;
        calculate, using the fraction (P(i)) and the mass fraction ($w_{ri}$), values ($V_{ri}$) which positively correlates with the mass fraction ($w_{ri}$) and negatively correlates with the fraction (P(i)); and
        determine the main ingredients according to the ingredients which have the values ($V_{ri}$) equal to or greater than a threshold value.

2. The system according to claim 1, wherein the controller is further configured to:
    sequence the values ($V_{ri}$) calculated for the each ingredient by size;
    determine largest difference between consecutive values in the sequence; and
    identify a pair of the consecutive values in the sequence corresponding to said largest difference, wherein the threshold value is equal to larger value of said pair.

3. The system according to claim 1, wherein the controller is further configured to calculate said values ($V_{ri}$) from the mass fraction ($w_{ri}$) and the fraction (P(i)) using formula: $V_{ri} = w_{ri} \log(P(i))$.

4. The system according to claim 1, wherein the controller is further configured to determine a parameter (Sim(r1, r2))

relating to similarity of food recipes based on the determined main ingredients and/or based on determined non-main ingredients of the respective food recipes, wherein the determined non-main ingredients are ingredients which are not the main ingredients of the respective food recipes.

5. The system according to claim 4, wherein said parameter (Sim(r1, r2)) is based on the determined main ingredients, and is defined by following formula:

$$\text{Sim}(r_1, r_2) = \frac{\sum_{k \text{ is main ingredient in } r_1 \text{ or } r_2} \min(w_{r_1 j}, w_{r_2 j}) \cdot \log(P(j))}{\sum_{k \text{ is main ingredient in } r_1 \text{ or } r_2} \max(w_{r_1 j}, w_{r_2 j}) \cdot \log(P(j))} \quad \text{(Formula 1)}$$

wherein $w_{r_1 j}$ and $w_{r_2 j}$ are mass fractions of the main ingredient j in the respective food recipes $r_1$ and $r_2$; P(j) is fraction of said population of known food recipes which uses the main ingredient.

6. The system according to claim 4, wherein said parameter (Sim(r1, r2)) is based on the determined non-main ingredients, and is defined by following formula:

$$\text{Sim}(r_1, r_2) = \frac{\sum_{k \text{ is non-main ingredient in } r_1 \text{ or } r_2} \min(w_{r_1 k}, w_{r_2 k}) \cdot \log(1 - P(k))}{\sum_{k \text{ is non-main ingredient in } r_1 \text{ or } r_2} \max(w_{r_1 k}, w_{r_2 k}) \cdot \log(1 - P(k))} \quad \text{(Formula 2)}$$

wherein $w_{r_1 k}$ and $w_{r_2 k}$ are mass fractions of the non-main ingredient k in the respective food recipes $r_1$ and $r_2$; P(k) is fraction of said population of known food recipes which uses the main ingredient k.

7. The system according to claim 4, wherein the controller is further configured to:
use a word similarity model to determine a similarity score for each pairwise combination of the determined main ingredients or the non-main ingredients of the respective recipes;
use the similarity score to identify pairs of main or non-main ingredients of the respective recipes; and
use a threshold of the similarity score to identify any unpaired main or non-main ingredients of the respective recipes.

8. The system according to claim 7, wherein said parameter (Sim($r_1$, $r_2$)) is based on the determined main ingredients, and is defined by following formula:

$$\text{Sim}(r_1, r_2) = \quad \text{(Formula 4)}$$

$$\frac{\sum_{l,m \text{ are paired main ingredients}} \min(w_{r_1 l}, w_{r_2 m}) \cdot \log(P(l) \cdot P(m)) \cdot \text{Sim}(l, m)}{\sum_{l,m \text{ are paired main ingredients}} \max(w_{r_1 l}, w_{r_2 m}) \cdot \log(P(l) \cdot P(m)) + 2 \sum_{n \text{ is unpaired main ingredient in } r_1 \text{ or } r_2} \max(w_{r_1 n}, w_{r_2 n}) \cdot \log(P(n))}$$

wherein $w_{r_1 l}$ is mass fraction of main ingredient l, paired with m, in recipe $r_1$; $w_{r_2 m}$ is mass fraction of main ingredient m, paired with c, in recipe $r_2$; P(l) is fraction of said population of known food recipes which uses the ingredient l; P(m) is fraction of said population of known food recipes which uses the ingredient m; Sim(l, m) is the similarity score for the paired main ingredients (l, m); $w_{r_1 n}$ and $w_{r_2 n}$ are mass fractions of unpaired main ingredient n in the respective recipes $r_1$ and $r_2$; P(n) is fraction of said population of known food recipes which uses the unpaired main ingredient n.

9. The system according to claim 7, wherein said parameter (Sim($r_1$, $r_2$)) is based on the determined non-main ingredients, and is defined by following formula:

$$\text{Sim}(r_1, r_2) = \quad \text{(Formula 5)}$$

$$\frac{\sum_{o,p \text{ are paired non-main ingredients}} \min(w_{r_1 l}, w_{r_2 m}) \cdot \log(P(l) \cdot P(m)) \cdot \text{Sim}(l, m)}{\sum_{o,p \text{ are paired non-main ingredients}} \max(w_{r_1 p}, w_{r_2 p}) \cdot \log((1 - P(o)) \cdot P(1 - (p))) + 2 \sum_{q \text{ is unpaired non-main ingredient in } r_1 \text{ or } r_2} \max(w_{r_1 q}, w_{r_2 q}) \cdot \log(1 - P(q))}$$

wherein $w_{r_1 o}$ is mass fraction of main ingredient o, paired with p, in recipe $r_1$; $w_{r_2 p}$ is mass fraction of non-main ingredient p, paired with o, in recipe $r_2$; P(o) is the fraction of said population of known food recipes which uses the ingredient o; P(p) is fraction of said population of known food recipes which uses the ingredient p; Sim(o, p) is the similarity score for the paired non-main ingredients (o, p); $w_{r_1 q}$ and $w_{r_2 q}$ are mass fractions of unpaired non-main ingredient q in the respective recipes $r_1$ and $r_2$; P(q) is fraction of said population of known food recipes which uses the unpaired non-main ingredient q.

10. A cooking appliance, comprising:
a heating element; and
the system according to claim 1, wherein the controller is configured to control the heating element based on the determined main ingredients and optionally based on masses of the determined main ingredients in the food recipe.

11. A computer implemented method for determining main ingredients of a food recipe, the method comprising:
receiving, via a user interface, an identity and mass fraction ($w_{ri}$) of each ingredient (i) in the food recipe (r);
receiving, from a database, the identity of ingredients of each known food recipe of a population of known food recipes;
calculating, for the each ingredient (i), fraction (P(i)) of said population of known food recipes which uses the ingredient;
calculating, using the fraction (P(i)) and the mass fraction ($w_{ri}$), values ($V_{ri}$) which positively correlates with the mass fraction ($w_{ri}$) and negatively correlates with the fraction (P(i)); and
determining the main ingredients according to the ingredients which have the values ($V_{ri}$) equal to or greater than a threshold value.

12. The method according to claim 11, further comprising: sequencing the values ($V_{ri}$) calculated for the each ingredient by size;
determining largest difference between consecutive values in the sequence; and identifying a pair of the consecutive values in the sequence corresponding to said largest difference, wherein the threshold value is equal to larger value of said pair.

13. The method according to claim 11, wherein the calculating said values ($V_{ri}$) from the mass fraction ($w_{ri}$) and the fraction ($P(i)$) uses formula:

$$V_{ri} = w_{ri} \log(P(i)).$$

14. The method according to claim 11, further comprising determining a parameter relating to similarity of recipes based on the determined main ingredients of the respective recipes and/or based on determined non-main ingredients of the respective food recipes, wherein the determined non-main ingredients are ingredients which are not the main ingredients of the respective food recipes.

15. A non-transitory computer readable medium comprising a computer program which is adapted, when said computer program is run on a computer, to implement the method of claim 11.

* * * * *